United States Patent
Oosawa et al.

(10) Patent No.: US 12,108,954 B2
(45) Date of Patent: Oct. 8, 2024

(54) ADHESION PROMOTION DEVICE

(71) Applicant: TERUMO KABUSHIKI KAISHA, Tokyo (JP)

(72) Inventors: Yuu Oosawa, Kanagawa (JP); Yuuki Hara, Kanagawa (JP); Wataru Karino, Kanagawa (JP); Naotaka Chino, Kanagawa (JP); Kei Honda, Kanagawa (JP); Takayuki Uchida, Kanagawa (JP); Masaru Ikegami, Kanagawa (JP); Xiaowei Lu, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 486 days.

(21) Appl. No.: 17/487,463

(22) Filed: Sep. 28, 2021

(65) Prior Publication Data
US 2022/0008080 A1    Jan. 13, 2022

Related U.S. Application Data

(63) Continuation of application No. PCT/JP2020/014071, filed on Mar. 27, 2020.

(30) Foreign Application Priority Data

Mar. 28, 2019  (JP) ................. 2019-064724

(51) Int. Cl.
*A61B 17/064*  (2006.01)
*A61B 17/08*  (2006.01)
*A61B 17/115*  (2006.01)
*A61B 17/00*  (2006.01)

(52) U.S. Cl.
CPC ........ *A61B 17/1155* (2013.01); *A61B 17/085* (2013.01); *A61B 2017/00884* (2013.01)

(58) Field of Classification Search
CPC .......................... A61B 17/068; A61B 17/1155
See application file for complete search history.

(56) References Cited

U.S. PATENT DOCUMENTS 9,055,944 B2 *  6/2015  Hodgkinson ...... A61B 17/3211
9,220,504 B2 * 12/2015  Viola ................... A61B 17/064
(Continued)

FOREIGN PATENT DOCUMENTS

JP      2003-533326 A   11/2003
JP      2006255411 A    9/2006
(Continued)

OTHER PUBLICATIONS

The extended European Search Report issued Apr. 5, 2022, by the European Patent Office in corresponding European Patent Application No. 20778484.4-1122. (10 pages).
(Continued)

*Primary Examiner* — Eyamindae C Jallow
(74) *Attorney, Agent, or Firm* — Buchanan Ingersoll & Rooney PC

(57) ABSTRACT

An adhesion promotion device is disclosed, which is capable of reducing risk factors of an anastomotic leakage after surgery. The adhesion promotion device has a main body portion disposed between biological organs serving as a joint object. The main body portion has a first region and a second region formed along an outer edge of the first region. The second region includes an adhesion promotion portion that promotes adhesion of a biological tissue. The first region includes a holding portion having a holding force with respect to the biological tissue which is stronger than that of the adhesion promotion portion.

19 Claims, 6 Drawing Sheets

(56) References Cited

U.S. PATENT DOCUMENTS

| | | | |
|---|---|---|---|
| 9,364,233 B2* | 6/2016 | Alexander, III | A61B 46/17 |
| 2005/0059996 A1 | 3/2005 | Bauman et al. | |
| 2006/0085030 A1 | 4/2006 | Bettuchi et al. | |
| 2006/0212050 A1 | 9/2006 | D'Agostino et al. | |
| 2006/0253094 A1 | 11/2006 | Hadba et al. | |
| 2009/0012543 A1 | 1/2009 | Kansoul | |
| 2011/0278346 A1 | 11/2011 | Hull et al. | |
| 2014/0097224 A1* | 4/2014 | Prior | A61B 17/105 227/176.1 |
| 2014/0197224 A1* | 7/2014 | Penna | A61B 17/115 227/179.1 |
| 2014/0239046 A1* | 8/2014 | Milliman | A61B 17/07292 227/176.1 |
| 2017/0281182 A1* | 10/2017 | Nativ | A61B 17/1155 |
| 2018/0214201 A1* | 8/2018 | Bargon | A61B 17/1114 |
| 2018/0325518 A1 | 11/2018 | Tannhauser et al. | |

FOREIGN PATENT DOCUMENTS

| | | |
|---|---|---|
| JP | 2007505708 A | 3/2007 |
| JP | 2008516669 A | 5/2008 |
| JP | 2009523480 A | 6/2009 |
| JP | 2011015966 A | 1/2011 |
| JP | 2013526342 A | 6/2013 |
| JP | 2016-540615 A | 12/2016 |
| WO | 01/89392 A2 | 11/2001 |

OTHER PUBLICATIONS

International Search Report (PCT/ISA/210) and Written Opinion (PCT/ISA/237) with translations mailed on May 19, 2020, by the Japan Patent Office as the International Searching Authority for International Application No. PCT/JP2020/014071.

English Translations of the International Search Report (Form PCT/ISA/210) and the Written Opinion of the International Searching Authority (Form PCT/ISA/237) issued May 19, 2020, by the Japanese Patent Office in corresponding International Application No. PCT/JP2020/014071. (7 pages).

Office Action (Notice of Reasons for Refusal) issued Jul. 4, 2023, by the Japan Patent Office in corresponding Japanese Patent Application No. 2021-509643 and an English translation of the Office Action. (8 pages).

* cited by examiner

ADHESION PROMOTION DEVICE

CROSS-REFERENCES TO RELATED APPLICATIONS

This application is a continuation of International Application No. PCT/JP2020/014071 filed on Mar. 27, 2020, which claims priority to Japanese Patent Application Publication No. 2019-064724 filed on Mar. 28, 2019, the entire content of both of which is incorporated herein by reference.

FIELD OF THE DISCLOSURE

The present disclosure generally relates to an adhesion promotion device.

BACKGROUND DISCUSSION

In the medical field, a medical procedure (for example, anastomosis for a digestive tract) of joining biological organs to each other by performing a surgical operation is known. In a case where the medical procedure as described above is performed, as a prognosis determinant after surgery, it is important that there is no delay in adhesion in a joint portion joined between the biological organs.

In the medical procedure of joining the biological organs, various methods and various medical instruments are used. For example, a method of suturing the biological organs by using a biodegradable suture, or a method of using a mechanical joining device (refer to Japanese Patent Application Publication No. 2007-505708 A) for performing anastomosis on the biological organs by using a stapler has been proposed. In particular, in a case where anastomosis is performed by using the mechanical joining device, compared to a method of using the suture, a joining force between the biological organs can be improved in the joint portion. Accordingly, risk factors of an anastomotic leakage can be reduced.

However, a degree of progress of adhesion in the joint portion depends on a state of biological tissues in a joint object site (joint target site) of a patient. Therefore, for example, even in a case where the joining device as disclosed in Japanese Patent Application Publication No. 2007-505708 A is used, depending on the state of the biological tissues of the patient, there is a possibility that the risk factors of the anastomotic leakage cannot be sufficiently reduced.

SUMMARY

An adhesion promotion device is disclosed, which is capable of reducing risk factors of an anastomotic leakage after a surgical operation is performed.

An adhesion promotion device is disclosed, which includes a main body portion disposed between biological organs serving as a joint object. The main body portion has a first region and a second region formed along an outer edge of the first region. The second region includes an adhesion promotion portion that promotes adhesion of a biological tissue. The first region includes a holding portion having a holding force with respect to the biological organs which is stronger than that of the adhesion promotion portion.

According to the adhesion promotion device of the present disclosure, the adhesion of the biological tissue of the biological organs can be promoted by pinching the main body portion between the biological organs serving as the joint object. In addition, while a medical procedure is performed, an operator uses the holding portion provided in the main body portion to increase the holding force of the main body portion for the biological organs serving as the joint object. In this manner, the main body portion can be prevented from falling out of the biological organs. Therefore, the operator can effectively reduce risk factors of an anastomotic leakage of the biological organs.

An adhesion promotion device is disclosed that promotes adhesion between biological tissue, the adhesion promotion device comprising: a main body portion made of biodegradable sheet that promotes adhesion of the biological tissue, the main body portion being disposed between biological organs serving as an object to be joined, the main body portion including a first region and a second region, the second region formed along an outer edge of the first region; the second region being formed of a biodegradable sheet having a plurality of through-holes that pass through the second region and includes an adhesion promotion portion that promotes adhesion of a biological tissue; and the first region includes one or more projections having a holding force with respect to the biological organs which is stronger than that of the adhesion promotion portion.

A method is disclosed of promoting adhesion between biological tissue comprising: disposing an adhesion promotion device including a sheet-shaped main body portion that promotes the adhesion of the biological tissue between one joint target sites and an other joint target site of an object to be joined of the biological organ; and joining the one joint target site and the other joint target site to each other in a state where at least a portion of the main body portion of the adhesion promotion device is disposed between the one joint target site and the other joint target site.

DETAILED DESCRIPTION

Figure 1A:
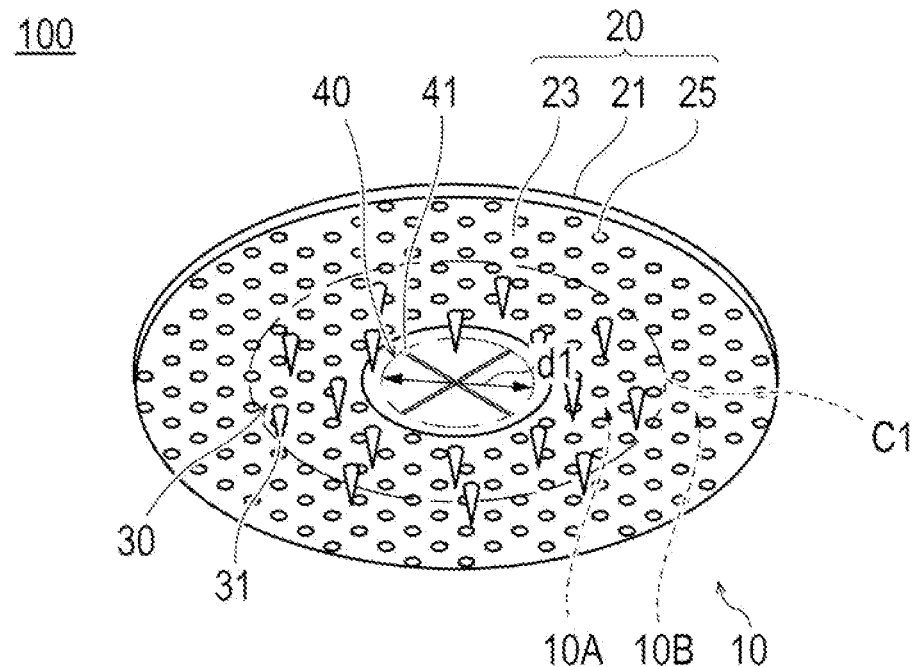
FIG. 1A is a perspective view when an adhesion promotion device according to an embodiment of the present disclosure is viewed from a rear surface side.

Set forth below with reference to the accompanying drawings is a detailed description of embodiments of an adhesion promotion device representing examples of the inventive adhesion promotion device disclosed here. In describing the drawings, the same reference numerals will be assigned to the same elements, and repeated description will be omitted. In addition, dimensional ratios in the drawings may be exaggerated for convenience of description, and may be different from actual ratios in some cases.

Figure 1B:
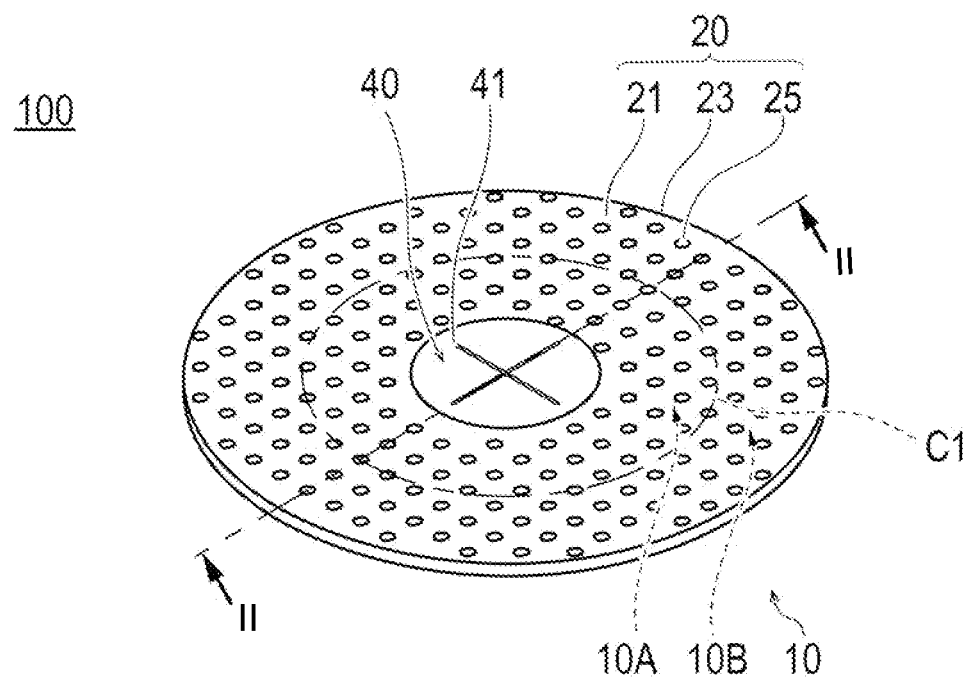
FIG. 1B is a perspective view when the adhesion promotion device according to the embodiment of the present disclosure is viewed from a front surface side.
Figure 2:
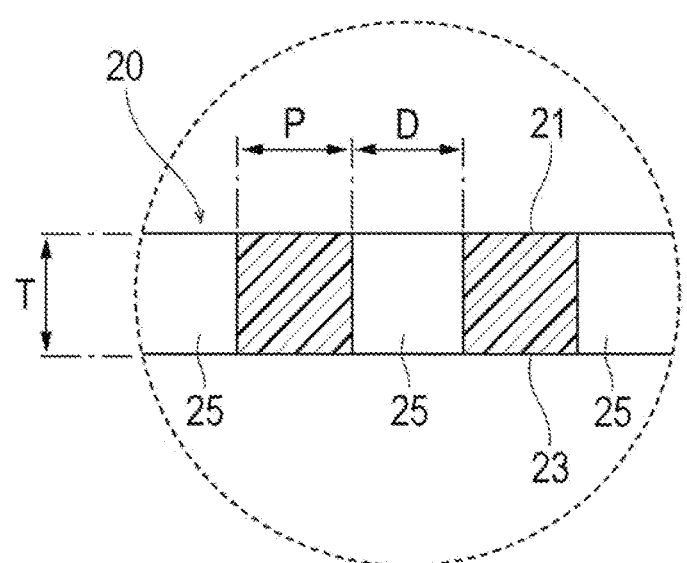
FIG. 2 is an enlarged cross-sectional view illustrating a portion of a cross section taken along line II-II in FIG. 1B.
Figure 3:
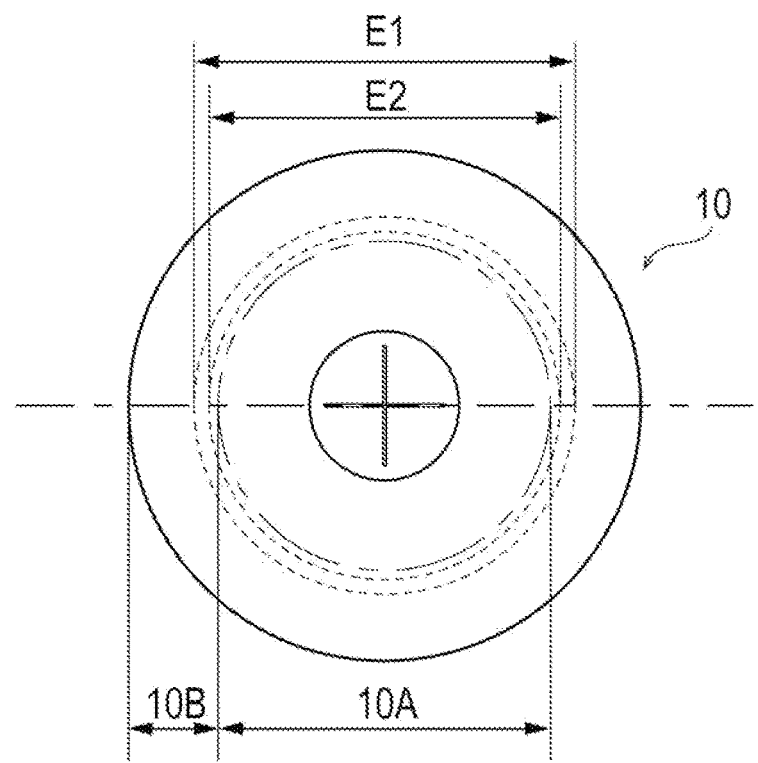
FIG. 3 is a plan view simply illustrating each region of the adhesion promotion device.

FIG. 1A is a perspective view when an adhesion promotion device 100 is viewed from a rear surface 23 side. FIG. 1B is a perspective view when the adhesion promotion device 100 is viewed from a front surface 21 side. FIG. 2 is an enlarged cross-sectional view illustrating a portion of a cross section taken along line II-II in FIG. 1B. FIG. 3 is a plan view simply illustrating each of regions 20A and 20B in the adhesion promotion device 100.

Adhesion Promotion Device 100

As illustrated in FIG. 1A, the adhesion promotion device 100 includes a main body portion 10 disposed between biological organs serving as a joint object. The main body portion 10 has a first region 10A and a second region 10B formed along an outer edge of the first region. The second region 10B includes an adhesion promotion portion 20 formed of a biodegradable sheet having a plurality of through-holes 25 and promoting adhesion of a biological tissue. The first region 10A includes a holding portion 30 having a holding force with respect to the biological organs which is stronger than that of the adhesion promotion portion 20.

As illustrated in FIGS. 7 to 10, the adhesion promotion device 100 is applicable to a medical procedure (for example, anastomosis for a digestive tract) in which predetermined biological organs are joined to each other. As will be described later, in describing the present specification, the large intestine anastomosis will be described as an example of the medical procedure of using the adhesion promotion device 100.

Main Body Portion 10

As illustrated in FIG. 1A, the main body portion 10 is configured to include a sheet-shaped member.

The main body portion 10 has the first region 10A and the second region 10B formed along the outer edge (i.e., outer diameter) of the first region 10A. The outer edge of the first region 10A is an imaginary line Cl in the drawing.

Each of Regions 10A and 10B

As illustrated in FIG. 1A, the first region 10A and the second region 10B of the main body portion 10 include the adhesion promotion portion 20 formed of the biodegradable sheet having the plurality of through-holes 25.

Figure 7:
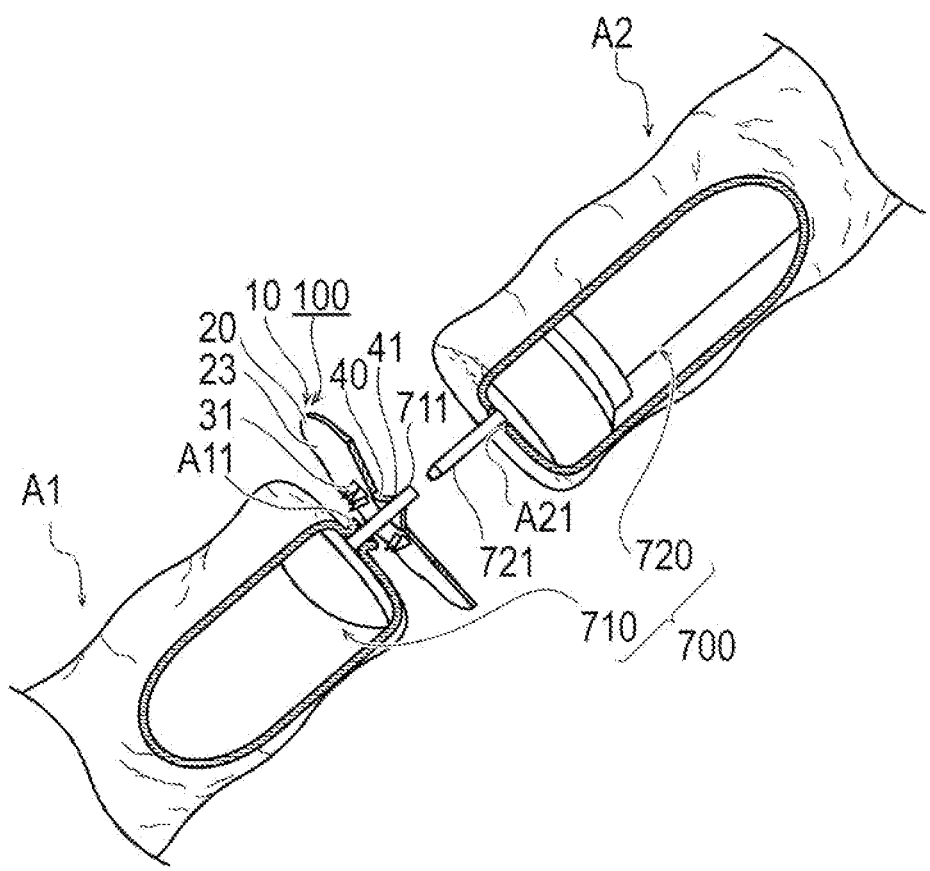
FIG. 7 is a schematic cross-sectional perspective view for describing the large intestine anastomosis.

In addition, as illustrated in FIGS. 1A and 7, the first region 10A further includes the holding portion 30 formed on a rear surface (i.e., back surface) 23 of the adhesion promotion portion 20, and an insertion portion 40 formed of an elastic member and into which a joining device 700 for joining the biological organs is inserted.

For example, the joining device 700 (medical instrument) for joining the biological organs can include an automatic anastomosis device including a first engagement instrument 710 and a second engagement instrument 720 (refer to FIGS. 7 to 10). For example, the first engagement instrument 710 and the second engagement instrument 720 are anvils and trocars. The main body portion 10 formed of the biodegradable sheet can be preferably used for a predetermined medical procedure.

Figure 8:
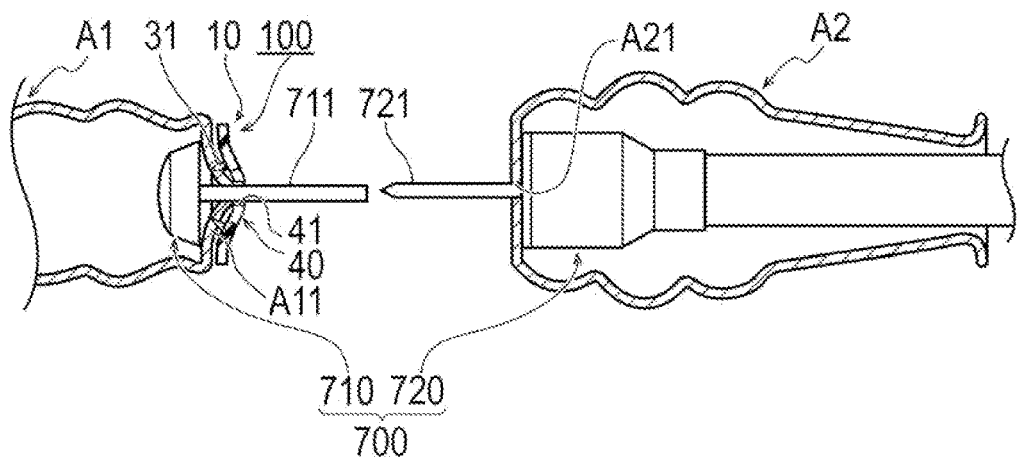
FIG. 8 is a schematic cross-sectional view for describing the large intestine anastomosis.

In a case where the main body portion 10 is used for the medical procedure of using the joining device 700, an operator (operator such as a doctor) sets each of the first engagement instrument 710 and the second engagement instrument 720 in the biological organs serving as the object to be joined (refer to FIG. 8). Then, the operator sets the main body portion 10 in the biological organs serving as the joint object by inserting the first engagement instrument 710 into the insertion portion 40 of the main body portion 10. Then, the operator causes the first engagement instrument 710 and the second engagement instrument 720 to engage with each other in a state where the main body portion 10 is set in the biological organs serving as the joint object (refer to FIG. 9). In this manner, the operator can dispose the main body portion 10 between the biological organs serving as the joint object.

In the medical procedure, in the main body portion 10, the holding portion 30 provided in the first region 10A of the main body portion 10 is at least partially caught on the biological organs serving as the joint object. In this manner, the holding force with respect to the biological organs can be increased. In this manner, the operator can help prevent the main body portion 10 from falling out of the biological organs due to misalignment of the main body portion 10.

In addition, in a state where the first engagement instrument 710 and the second engagement instrument 720 engage with each other, the operator causes the joining device 700 to puncture and excise a portion of the biological organ pinched by the joining device 700 and a portion of the main body portion 10. In addition, the operator causes the joining device 700 to excise each configuration member pinched by the joining device 700, and joins peripheries of the excised site at the same time. Then, the joining device 700 is removed outward of a living body (refer to FIG. 10).

Figure 10:
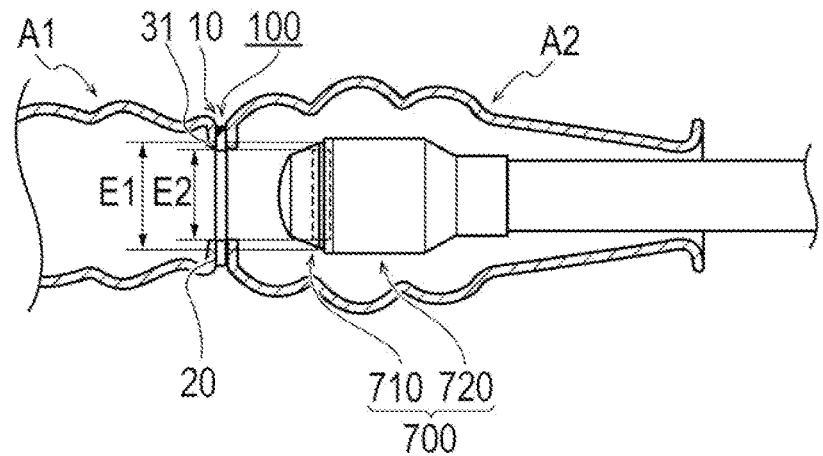
FIG. 10 is a schematic cross-sectional view for describing the large intestine anastomosis.

In the medical procedure, the joining device 700 punches each configuration member pinched by the joining device 700 by using a punching blade incorporated in the first engagement instrument 710 or the second engagement instrument 720. Therefore, as illustrated in FIGS. 3 and 10, a region E2 where the biological organ joined by the joining device 700 is punched is located inward of a region E1 where the first engagement instrument 710 and the second engagement instrument 720 face and overlap each other across the main body portion 10.

In addition, as illustrated in FIGS. 1A and 3, the first region 10A of the main body portion 10 is located inward of the region E1 where the first engagement instrument 710 and the second engagement instrument 720 face and overlap each other across the main body portion 10. According to this configuration, in a state where the operator pinches the main body portion 10 between the first engagement instrument 710 and the second engagement instrument 720, when the main body portion 10 pinched by the joining device 700 is punched, the operator can remove most of the holding portion 30. In addition, when the operator removes the joining device 700 outward of the living body, the operator can remove most of the holding portion 30 provided in the first region 10A of the main body portion 10 outward of the living body. For example, in a case where the holding portion 30 is formed of a biodegradable material, in the above-described medical procedure, at least a portion of the holding portion 30 may indwell the living body after the main body portion 10 is punched by the joining device 700. In a case where the holding portion 30 is formed of the biodegradable material, the holding portion 30 is degraded and absorbed inside the living body.

It is preferable that the first region 10A of the main body portion 10 is formed of a biodegradable sheet. However, a material thereof is not particularly limited as long as the first region 10A can be disposed in the biological organ and further has the holding portion. Most of the first region 10A of the main body portion 10 is punched by the joining device 700. Accordingly, as illustrated in FIG. 1A, the first region 10A may not be formed by the adhesion promotion portion 20.

As illustrated in FIGS. 1A and 3, it is preferable that the first region 10A of the main body portion 10 is located inward of the region E2 where the biological organ joined by the joining device 700 is punched. According to this configuration, when the joining device 700 is removed outward of the living body, all of the holding portion 30 provided in the first region 10A of the main body portion 10 can be removed outward of the living body. In this manner, even in a case where the holding portion 30 is formed of a non-biodegradable material, it is possible to reduce a possibility that foreign substances may indwell the body.

On the other hand, as illustrated in FIG. 1A, only the adhesion promotion portion 20 is provided in the second region 10B of the main body portion 10. In the above-described medical procedure, in a state of being pinched between the first engagement instrument 710 and the second engagement instrument 720, the second region 10B of the main body portion 10 indwells the living body after being joined by the joining device 700 and the main body portion 10 is punched by the joining device 700. Therefore, the main body portion 10 can reliably fulfil a function of promoting adhesion with respect to the biological organs serving as the joint object by using the adhesion promotion portion 20 provided in the second region 10B of the main body portion 10.

Adhesion Promotion Portion 20

As illustrated in FIGS. 1A and 1B, each of the through-holes 25 formed in the adhesion promotion portion 20 is regularly and periodically provided in a surface direction of the adhesion promotion portion 20. However, each of the through-hole 25 may be randomly provided in each portion in the surface direction of the adhesion promotion portion 20.

As illustrated in FIG. 2, each of the through-holes 25 extends substantially perpendicular between the front surface 21 and the rear surface 23 along a thickness direction (upward-downward direction in FIG. 2) of the adhesion promotion portion 20. Each of the through-holes 25 may be bent or curved in a zigzag manner between the front surface 21 and the rear surface 23, in a cross section taken along the thickness direction of the adhesion promotion portion 20.

Each of the through-holes 25 has a substantially circular planar shape (shape when the front surface 21 of the adhesion promotion portion 20 or the rear surface 23 of the adhesion promotion portion 20 is viewed in a plan view). However, the planar shape of each of the through-holes 25 is not particularly limited, and may be an elliptical shape or a polygonal shape (rectangular shape or triangular shape), for example. In addition, each of the through-holes 25 may have a different planar shape or cross-sectional shape.

The adhesion promotion portion 20 has a substantially circular planar shape. However, the planar shape of the adhesion promotion portion 20 is not particularly limited, and may be an elliptical shape or a polygonal shape (rectangular shape or triangular shape), for example.

A thickness (dimension T illustrated in FIG. 2) of the adhesion promotion portion 20 is not particularly limited. However, the thickness, for example, can be 0.05 mm to 0.3 mm, and is preferably 0.1 mm to 0.2 mm. In a case where the thickness of the adhesion promotion portion 20 is 0.05 mm or larger (for example, in a case where the thickness is 0.1 mm or larger), the adhesion promotion portion 20 can be provided with strength to such an extent that the adhesion promotion portion 20 is not damaged when the adhesion promotion device 100 is handled. In a case where the thickness of the adhesion promotion portion 20 is 0.3 mm or smaller (for example, when the thickness is 0.2 mm or smaller), the adhesion promotion portion 20 can be provided with sufficient flexibility to follow the biological tissue after the adhesion promotion portion 20 closely adheres to the biological tissue to which the adhesion promotion portion 20 is applied.

In accordance with an exemplary embodiment, the adhesion promotion portion 20 has a ratio value of hole diameter D (distance D illustrated in FIG. 2) of the through-hole 25 with respect to a pitch P (distance P illustrated in FIG. 2 and a distance between the through-holes 25 adjacent to each other) of the through-holes 25, for example, that is 0.25 or greater and smaller than 40. In a case where the planar shape of the through-hole 25 is a perfect circle, the hole diameter D of the through-hole 25 is equal to a diameter of the perfect circle. In a case where the planar shape of the through-hole 25 is not a perfect circle, the diameter of the perfect circle (diameter corresponding to a circle) having an area the same as an area of an opening portion (portion facing the front surface 21 or the rear surface 23 in the through-hole 25) of the through-hole 25 can be defined as the hole diameter D of the through-hole 25.

The adhesion promotion portion 20 includes the plurality of through-holes 25. Accordingly, a plurality of values exist for the hole diameter D corresponding to each of the through-holes 25. Therefore, in the present embodiment, in calculating the above-described ratio value, an arithmetic mean value of two or more values of the hole diameter D corresponding to each of the plurality of the through-holes 25 is used as a representative value of the hole diameter D. The pitch P of the plurality of through-holes 25 is defined by a shortest distance between the opening portions of the two through-holes 25. However, with regard to the value of the pitch P, a plurality of values exist in the pitch P corresponding to a combination of the through-holes 25 adjacent to each other. Therefore, in the present embodiment, in calculating the above-described ratio value, the arithmetic mean value of two or more values of the pitch P corresponding to each combination of the through-holes 25 adjacent to each other is used as the representative value of the pitch P.

The pitch P, the hole diameter D, and the ratio of the hole diameter D with respect to the pitch P of the through-hole 25 are examples, and the configuration is not limited to the pitch P, the hole diameter D, and the ratio of the hole diameter D with respect to the pitch P of the through-hole 25 as disclosed.

The adhesion promotion portion 20 can be formed of a biodegradable material. The material of the adhesion promotion portion 20 is not particularly limited, and the material of the adhesion promotion portion 20 can include a biodegradable resin, for example. For example, as the biodegradable resin of the material of the adhesion promotion portion 20 can include degradable (co)polymers disclosed in Japanese Patent Application Publication No. 2011-528275 A, Japanese Patent Application Publication No. 2008-514719 A, Pamphlet of International Publication No. 2008-1952 (i.e., WO 2008/001952), or Japanese Patent Application Publication No. 2004-509205 A. Specifically, for example, the biodegradable resin includes (1) a polymer selected from a group consisting of aliphatic polyester, polyester, polyacid anhydride, polyorthoester, polycarbonate, polyphosphazene, polyphosphate ester, polyvinyl alcohol, polypeptide, polysaccharide, protein, and cellulose, and (2) a copolymer formed of one or more monomers forming (1) described above. That is, it is preferable that the biodegradable sheet includes at least one type of the biodegradable resin selected from the group consisting of the polymer selected from the group consisting of aliphatic polyester, polyester, polyacid anhydride, polyorthoester, polycarbonate, polyphosphazene, polyphosphate ester, polyvinyl alcohol, polypeptide, polysaccharide, protein, and cellulose, and the copolymer formed of one or more monomers forming the polymer.

A method for manufacturing the adhesion promotion portion 20 is not particularly limited. For example, the method for manufacturing the adhesion portion 20 can include a method for preparing a fiber formed of the above-described biodegradable resin and manufacturing a mesh-shaped sheet by using the fiber. The method for preparing the fiber formed of the biodegradable resin is not particularly limited. For example, the method for preparing the fiber formed of the biodegradable resin can include an electrospinning method (electrospinning method and electrostatic spinning method) and a melt blow method. For the adhesion promotion portion 20, only one of the above-described methods may be selected and used, or two or more of the above-described methods may be selected and appropriately combined with each other. As still another example of the method for manufacturing the adhesion promotion portion 20, the biodegradable sheet according to the present invention may be manufactured by spinning the fiber formed of the above-described biodegradable resin in accordance with a usual method in the related art and knitting the obtained fiber into a mesh shape.

The adhesion promotion portion 20 induces a biological reaction by a forming material such as the biodegradable resin forming the adhesion promotion portion 20. The adhesion promotion portion 20 induces expression of a biological component such as fibrin by the action. The biological component induced by the adhesion promotion portion can promote the adhesion by being accumulated to penetrate the through-hole 25 of the adhesion promotion portion 20. Therefore, the adhesion promotion portion 20 formed in the main body portion 10 of the adhesion promotion device 100 is disposed between the biological organs serving as the joint object. In this manner, the adhesion is promoted by the above-described mechanism.

The material of adhesion promotion portion 20 may not be biodegradable as long as the adhesion can be promoted. In addition, the adhesion promotion portion 20 may not have the through-hole 25 regardless of the material, as long as the adhesion can be promoted.

Holding Portion 30

As illustrated in FIG. 1A, the holding portion 30 is provided in the first region 10A of the main body portion 10. The adhesion promotion portion 20 is provided in the first region 10A of the main body portion 10, and the holding portion 30 is provided in the rear surface 23 of the adhesion promotion portion 20. In addition, the holding portion 30 has a plurality of projections 31. The plurality of the projections 31 applies a holding force with respect to the biological organ to the main body portion 10 by disposing the main body portion 10 in the biological organ serving as the joint object.

In accordance with an exemplary embodiment, as illustrated in FIG. 1A, the plurality of the projections 31 are conical projections. The plurality of the projection 31 utilizes a conical shape of each of the projections 31. In this manner, sliding resistance (friction resistance) can be at least partially generated for the biological organ serving as the joint object. According to this configuration, the main body portion 10 can increase the holding force with respect to the biological organ by the plurality of projections 31. In this manner, an operator can help prevent the adhesion promotion device 100 from falling out of the biological organ while a medical procedure is performed.

A distal end of the plurality of conical projections 31 can partially penetrate a front surface tissue of the biological organ serving as the joint object. Therefore, the plurality of the projections 31 can more reliably generate the sliding resistance with respect to the biological organ serving as the joint object.

A cross-sectional shape of each of the projections 31 is not particularly limited as long as the shape is a projection shape. For example, the projection 31 can be formed in a polygonal shape such as a triangular shape and a trapezoidal shape, a dome shape, or a branch shape in which the shapes are combined with each other.

In addition, a size of each of the plurality of projections 31 is not particularly limited. As illustrated in FIG. 1A, the size of each of the plurality of projections 31 may be constant (i.e., same), or may be irregular (i.e., different).

As illustrated in FIG. 1A, the plurality of projections 31 are regularly (i.e., equally spaced apart) provided with respect to a center position of the main body portion 10 in the surface direction of the main body portion 10. According to this configuration, the holding portion 30 provided in the first region 10A of the main body portion 10 can equally apply the holding force with respect to the biological organ in the surface direction of the main body portion 10.

Each disposition (i.e., location) of the plurality of projections 31 is not particularly limited. For example, each of the plurality of projections 31 may be irregularly provided (i.e., randomly spaced apart), instead of being regularly provided with respect to the center position of the main body portion 10 in the surface direction of the main body portion 10.

In addition, for example, each of the plurality of projections 31 can be formed of the biodegradable resin, a thermoplastic elastomer, a thermoplastic resin such as nylon and PET, or metal such as a stainless steel wire (SUS wire), a copper wire, a titanium wire, and a nitinol wire. The material of each of the plurality of projections 31 is not particularly limited as long as each of the plurality of projections 31 can be caught on the biological organ in a state where the main body portion 10 is disposed in the biological organ serving as the joint object, and the holding force of the main body portion 10 can be increased for the biological organ.

In addition, the method of preparing the plurality of projections 31 is not particularly limited. The holding portion 30 configured to include the plurality of projections 31 may be integrally formed on the outer surface of the main body portion 10, or may be molded separately from the main body portion 10 to be connected to the main body portion 10 by covering the outer surface of the main body portion 10. In this manner, a preparing method suitable for the forming material of the holding portion 30 can be adopted.

In addition, an example has been described in which the number of the projections 31 is two or more. However, the number of the projections 31 may be one.

In addition, the projection 31 may have a hook shape for preventing slippage.

Insertion Portion 40

As illustrated in FIGS. 1A and 1B, the insertion portion 40 is provided at a center position of the first region 10A of the main body portion 10. In addition, an insertion hole 41 into which the joining device 700 is inserted is provided at the center position of the insertion portion 40.

As illustrated in FIGS. 1A and 1B, the insertion portion 40 can have a substantially circular planar shape. However, the planar shape of the insertion portion 40 is not particularly limited, and may be an elliptical shape or a polygonal shape (rectangular shape or triangular shape), for example. In addition, the insertion portion 40 may be disposed at any position in the first region 10A of the main body portion 10.

As illustrated in FIGS. 1A and 1B, the insertion portion 40 includes the insertion hole 41 penetrating the main body portion 10 in the thickness direction. The insertion portion 40 is formed of an elastic material, and can be at least partially deformed along a direction in which the joining device 700 is inserted into the insertion hole 41 (refer to FIG. 7). According to this configuration, the insertion portion 40 can at least partially generate the sliding resistance in the joining device 700. Therefore, the main body portion 10 can increase the holding force with respect to the joining device 700 inserted into the insertion hole 41 by the insertion portion 40. Therefore, the operator can help prevent the adhesion promotion device 100 from falling out of the joining device 700 while the medical procedure is performed.

As illustrated in FIGS. 1A and 1B, the insertion hole 41 can have a cross-cut shape. An imaginary hole diameter dl connecting outer edges of the insertion hole 41 can be formed to be 5 mm to 25 mm, for example. The planar shape of the insertion hole 41 is not limited to the cross-cut shape. The planar shape of the insertion hole 41 is not particularly limited as long as the planar shape is substantially the same as that of the joining device 700 inserted into the insertion hole 41, or a shape that can at least partially generate the sliding resistance with respect to the joining device 700 inserted into the insertion hole 41 and can increase the holding force of the main body portion 10 for the joining device 700. In addition, the insertion hole 41 may be disposed at any position in the insertion portion 40.

For example, the insertion portion 40 can be formed of rubber or silicone elastomer. A material of the insertion portion 40 is not particularly limited as long as the insertion portion 40 can at least partially generate the sliding resistance with respect to the joining device 700, when the operator sets the main body portion 10 in the biological organ serving as the joint object by inserting the joining device 700 into the insertion hole 41.

In addition, a method of preparing the insertion portion 40 is not particularly limited. The insertion portion 40 may be formed integrally with the outer surface of the main body portion 10, or may be molded separately from the main body portion 10 to be connected to the outer surface of the main body portion 10. In this manner, a preparing method suitable for the forming material of the insertion portion 40 can be adopted.

In addition, the method of preparing the insertion hole 41 is not particularly limited. The insertion hole 41 may be prepared in advance when the insertion portion 40 is prepared, or may be prepared by the operator while the medical procedure is performed.

In addition, without being limited to the joining device 700 that joins the biological organs, a medical instrument that can be inserted into the insertion hole 41 is not particularly limited.

As described above, the adhesion promotion device 100 according to the present embodiment has the main body portion 10 disposed between the biological organs serving as the joint object. The main body portion 10 has the first region 10A and the second region 10B formed along the outer edge of the first region. The second region 10B includes the adhesion promotion portion 20 that promotes the adhesion of the biological tissue. The first region 10A includes the holding portion 30 having the holding force with respect to the biological organ which is stronger than that of the adhesion promotion portion 20.

According to the adhesion promotion device 100 as described above, the holding portion 30 provided in the first region 10A of the main body portion 10 can at least partially generate the sliding resistance with respect to the biological organ serving as the joint object. Therefore, the main body portion 10 can increase the holding force with respect to the biological organ serving as the joint object by the holding portion 30. Therefore, the operator can help prevent the main body portion 10 from falling out of the biological organ while the medical procedure is performed, and can effectively reduce risk factors of an anastomotic leakage of the biological organ. In addition, the adhesion promotion portion 20 provided in the second region 10B of the main body portion 10 can promote the adhesion of the biological organs by accumulating the biological component of the biological organ serving as the joint object in the through-hole 25.

The holding portion 30 is integrally formed at a portion of the outer surface of the main body portion 10. Alternatively, the holding portion 30 is formed separately from the main body portion 10, and is connected to a portion of the outer surface of the main body portion 10 while covering the portion of the outer surface of the main body portion 10. According to this configuration, a preparing method suitable for the forming material of the holding portion 30 can be adopted.

The holding portion 30 includes at least one of the projections 31. According to this configuration, the distal end of the projection 31 can partially penetrate a front surface tissue of the biological organ serving as the joint object. Therefore, the holding portion 30 can reliably generate the sliding resistance with respect to the biological organ serving as the joint object. Therefore, while the medical procedure is performed, the operator can help prevent the adhesion promotion device 100 from falling out of the biological organ, and can effectively reduce the risk factors of the anastomotic leakage of the biological organ.

The main body portion 10 further has the insertion portion 40 formed of the elastic member, and the insertion portion 40 further has the insertion hole 41 into which the joining device 700 is inserted. According to this configuration, the insertion portion 40 can be at least partially deformed along the direction in which the joining device 700 is inserted into the insertion hole 41. In this manner, the insertion portion 40 can at least partially generate the sliding resistance with respect to the joining device 700 inserted into the insertion hole 41. Therefore, the main body portion 10 can increase the holding force with respect to the inserted joining device 700 by the insertion portion 40. Therefore, while the medical procedure is performed, the operator can help prevent the adhesion promotion device 100 from falling out of the joining device 700, and can effectively reduce the risk factors of the anastomotic leakage of the biological organ.

In accordance with an exemplary embodiment, the main body portion 10 is disposed in one joint target site of the biological organ serving as the joint object, and the second region 10B is joined to the biological tissue by the medical instrument including the first engagement instrument 710 disposed in one joint target site of the biological organ, and the second engagement instrument 720 disposed in the other joint site of the biological organ and facing the first engagement instrument 710. In addition, when the main body portion 10 is joined to the biological tissue by the first engagement instrument 710 and the second engagement instrument 720, the first region 10A is located inward of the region E1 where the first engagement instrument 710 and the second engagement instrument 720 face and overlap each other across the main body portion 10. According to this configuration, while the joining device 700 punches and excises a portion of the biological organ pinched by the joint portion of the joining device 700 and a portion of the main body portion 10, the joining device 700 joins peripheries of the excised site. When the joining device 700 is removed outward of the living body, most of the holding portion 30 can be removed outward of the living body. Therefore, even when the holding portion 30 is formed of a non-biodegradable material, it is possible to reduce a possibility that foreign substances may indwell the body.

Hitherto, the adhesion promotion device 100 has been described with reference to the embodiment. However, the present disclosure is not limited to the description of the above-described embodiment, and various modifications can be made within the scope not departing from the concept. In the following description, modification examples of the holding portion 30 will be described. In describing the modification examples, configurations and contents which are described above in the adhesion promotion device 100 will be appropriately omitted in the description. In addition, the contents not particularly described in the modification examples can be regarded as the same as those in the above-described embodiment.

Modification Example 1

Figure 4A:
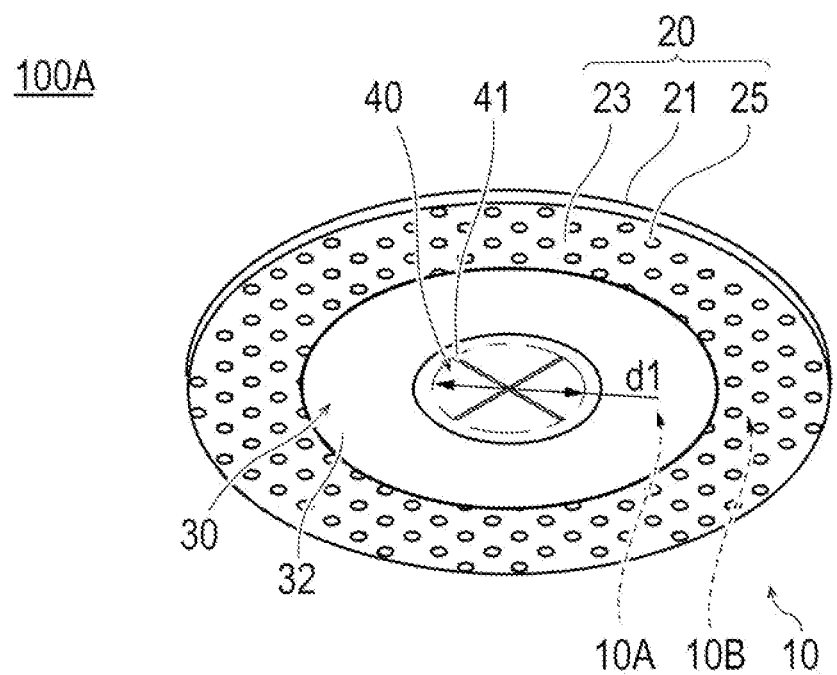
FIG. 4A is a perspective view illustrating a modification example of a holding portion in the adhesion promotion device.
Figure 4B:
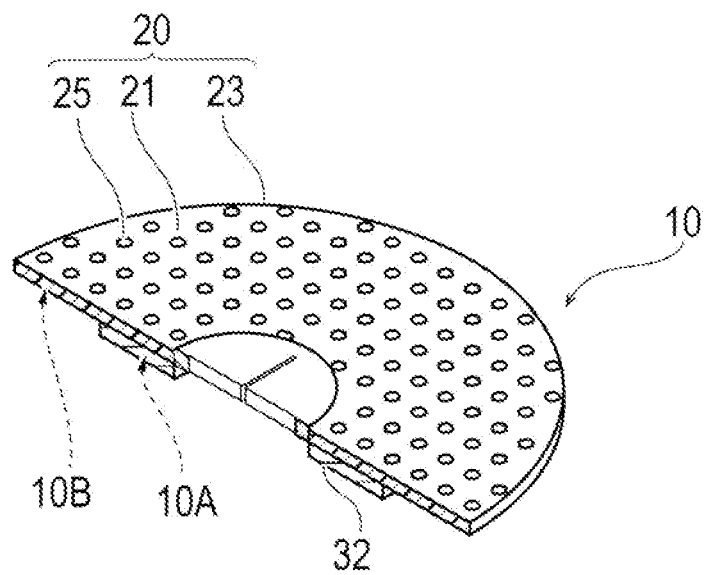
FIG. 4B is a cross-sectional view illustrating a modification example of the holding portion in the adhesion promotion device.

FIG. 4A is a perspective view illustrating a modification example of the holding portion in an adhesion promotion device 100A. FIG. 4B is a cross-sectional view illustrating the modification example of the holding portion in the adhesion promotion device 100A.

As illustrated in FIGS. 4A and 4B, the adhesion promotion device 100A has the main body portion 10 disposed between the biological organs serving as the joint object. The main body portion 10 has the first region 10A and the second region 10B formed along the outer edge of the first region. The second region 10B includes the adhesion promotion portion 20 formed of a biodegradable sheet having the plurality of through-holes 25 and promoting the adhesion of the biological tissue. The first region 10A has a holding portion 30A having the holding force with respect to the biological organ which is stronger than that of the adhesion promotion portion 20, and the insertion portion 40 that can increase the holding force of the main body portion 10 for the joining device 700. The insertion portion 40 includes the insertion hole 41 into which the joining device 700 is inserted.

As illustrated in FIGS. 4A and 4B, the holding portion 30A has a friction portion 32 disposed in the biological organ serving as the joint object so that the holding force with respect to the biological organ is applied to the main body portion 10.

For example, the friction portion 32 can be formed of a coating agent such as a resin layer to which a particulate substance is added, and can generate the sliding resistance with respect to the biological organ serving as the joint object. Therefore, while the medical procedure is performed, the operator can prevent the adhesion promotion device 100 from falling out of the biological organ, and can effectively reduce the risk factors of the anastomotic leakage of the biological organ.

A material of the friction portion 32 is not particularly limited. The friction portion 32 can be formed of a material that can at least partially generate the sliding resistance with respect to the front surface tissue of the biological organ serving as the joint object, and can increase the holding force of the main body portion 10 for the biological organ. In addition, a cross-sectional shape of the friction portion 32 is not limited to a configuration including a projection shape, and is not particularly limited.

In addition, disposition of the friction portion 32 is not particularly limited. For example, as illustrated in FIGS. 4A and 4B, the friction portion 32 may be entirely provided in the first region 10A of the main body portion 10, or may be partially provided in the first region 10A of the main body portion 10. [0091] In addition, a method of preparing the friction portion 32 is not particularly limited. The friction portion 32 may be integrally formed on the outer surface of the main body portion 10, or may be molded separately from the main body portion 10 to be connected to the main body portion 10 by covering the outer surface of the main body portion 10. In this manner, a preparing method suitable for the forming material of the friction portion 32 can be adopted. In addition, the thickness of the friction portion 32 is not particularly limited.

Hitherto, an example of the configuration of the adhesion promotion device has been described. However, a specific configuration thereof is not limited as long as the main body portion 10 of the adhesion promotion device 100 according to the present invention has the holding portion 30. For example, the holding portion 30 may be configured so that the one or more projections 31 and the friction portion 32 are appropriately combined with each other. In addition, the main body portion 10 may have the hole portion without having the insertion portion 40. The hole portion may be prepared in advance in the main body portion 10, or may be prepared by the operator while the medical procedure is performed. The operator can select various modifications of the main body portion 10 in accordance with a progress of the medical procedure.

Embodiment of Treatment Method (Biological Organ Anastomosis)

Next, a treatment method of using the adhesion promotion device will be described.

Figure 5:
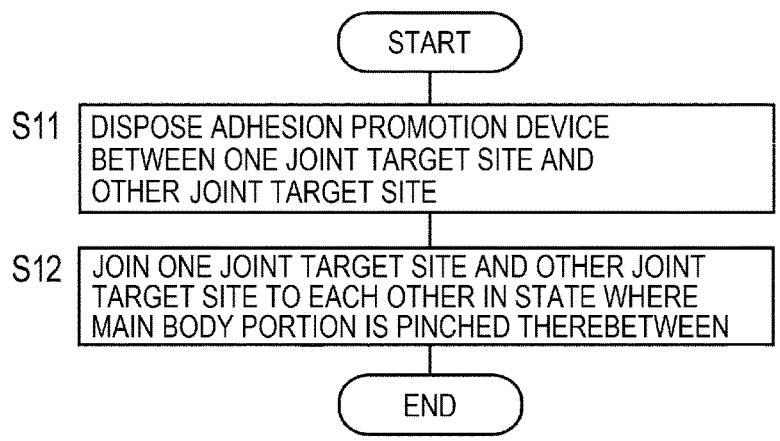
FIG. 5 is a flowchart illustrating each procedure of a treatment method of using the adhesion promotion device.

FIG. 5 is a flowchart illustrating each procedure of the treatment method of using the adhesion promotion device.

The treatment method can include disposing the adhesion promotion device including the sheet-shaped main body portion that promotes the adhesion of the biological tissue between one joint target sites and the other joint target site of the joint object of the biological organ (S11), and joining one joint target site and the other joint target site to each other in a state where at least a portion of the main body portion of the adhesion promotion device is disposed between one joint target site and the other joint target site (S12).

The biological organs joined by using the treatment method and the joint target site in the biological organs are not particularly limited, and can be selected in any desired manner. However, in the following description, large intestine anastomosis will be described as an example. In addition, as the adhesion promotion device used in each medical procedure described below, for example, any desired device can be selected from the above-described adhesion promotion devices. However, in the following description, as a representative example that can be preferably used for each medical procedure, an application example of the adhesion promotion device 100 illustrated in FIG. 1 will be described.

In addition, in each medical procedure described below, detailed description of a known medical procedure or a known joining device will be appropriately omitted.

Hereinafter, in the description in the present specification, "disposing the adhesion promotion device between the biological organs" means at least any one of disposing the adhesion promotion device in a state of being in direct or indirect contact with the biological organs, disposing the adhesion promotion device in a state where a spatial gap is formed between the adhesion promotion device and the biological organs, and disposing the adhesion promotion device in both the states (for example, disposing the adhesion promotion device in a state where the adhesion promotion device is in contact with one biological organ and the adhesion promotion device is not in contact with the other biological organ). In addition, in the description in the present specification, a "periphery" does not define a strict range (region), and means a predetermined range (region) as long as a treatment purpose (joining the biological organs to each other) can be achieved. In addition, as long as the treatment purpose can be achieved, in the medical procedure described in each treatment method, orders of the medical procedures can be appropriately switched among the medical procedures. In addition, in the description in the present specification, "moving the portions to be relatively closer to each other" means both moving two or more objects to be closer to each other, and moving only one to be closer to the other one.

Embodiment of Treatment Method (Large Intestine Anastomosis)

Figure 6:
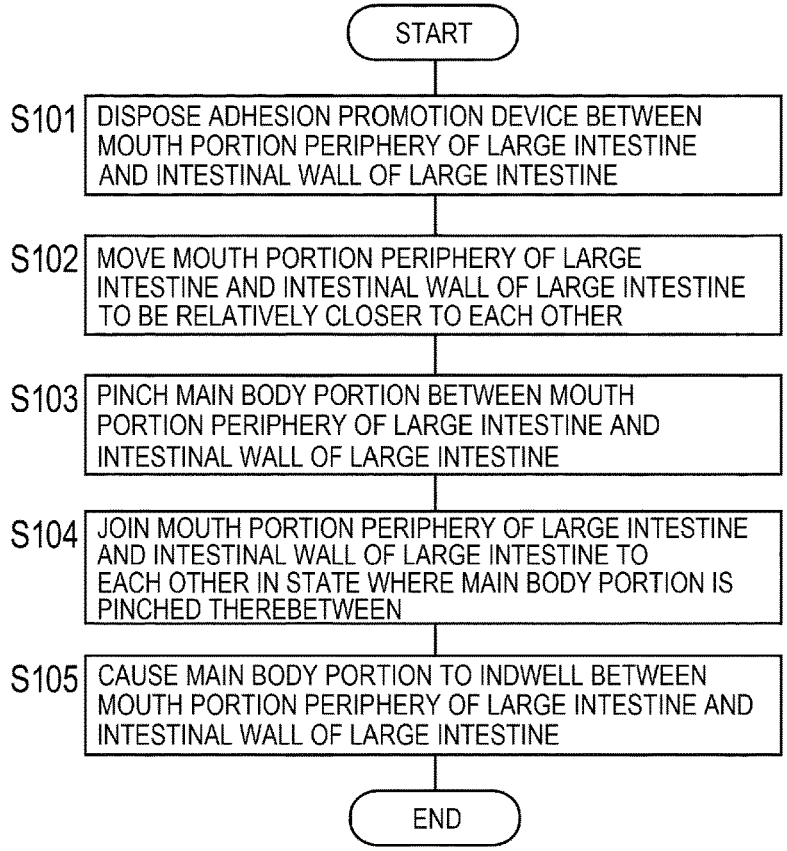
FIG. 6 is a flowchart illustrating a procedure of an embodiment (large intestine anastomosis) of the treatment method.

FIG. 6 is a flowchart illustrating a procedure of an embodiment of the treatment method (large intestine anastomosis), and FIGS. 7 to 10 are views for describing the large intestine anastomosis.

In the treatment method according to the present embodiment, the biological organ serving as the joint object is a large intestine cut due to excision of a cancer tumor. Specifically, the biological organs serving as the joint object are a mouth side A1 of the cut large intestine and an anal side A2 of the cut large intestine. In the following description, a procedure will be described in which a mouth portion periphery (one joint target site) on the mouth side A1 of the cut large intestine and a portion (other joint target site) of an intestinal wall on the anal side A2 of the cut large intestine are joined to each other.

As illustrated in FIG. 6, the treatment method according to the present embodiment includes disposing the adhesion promotion device 100 between the mouth portion periphery of the large intestine and the intestinal wall of the large intestine (S101), moving the mouth portion periphery of the large intestine and the intestinal wall of the large intestine to be relatively closer to each other (S102), pinching the main body portion 10 of the adhesion promotion device 100 between the mouth portion periphery of the large intestine and the intestinal wall of the large intestine (S103), joining the mouth portion periphery of the large intestine and the intestinal wall of the large intestine to each other in a state where the main body portion 10 of the adhesion promotion device 100 is pinched between the mouth portion periphery of the large intestine and the intestinal wall of the large intestine (S104), and causing the main body portion 10 of the adhesion promotion device 100 to indwell between the mouth portion periphery of the large intestine and the intestinal wall of the large intestine (S105). [0103] Next, the treatment method according to the present embodiment will be described with reference to FIGS. 7 to 10.

As illustrated in FIG. 7, the operator inserts the first engagement instrument 710 of the joining device 700 into the mouth side A1 of the large intestine. The operator disposes the second engagement instrument 720 of the joining device 700 on the anal side A2 of the large intestine. Before the second engagement instrument 720 is disposed on the anal side A2 of the large intestine, the operator forms a through-hole A21 for inserting the second engagement instrument 720 of the joining device 700 into the anal side A2 of the large intestine. A timing at which the through-hole A21 is formed is not particularly limited as long as the timing is before the second engagement instrument 720 is disposed.

For example, as the joining device 700, a known device used for the large intestine anastomosis can be used. As the first engagement instrument 710 and the second engagement instrument 720 engage with each other, the joining device 700 excises the biological tissue disposed between the first engagement instrument 710 and the second engagement instrument 720, and sutures a periphery of the excised biological tissue into a circumferential shape by using a stapler. For example, the first engagement instrument 710 is an instrument including a cylindrical engagement target portion 711. For example, the second engagement instrument 720 is an instrument including an engagement pin 721 to engage with and to be inserted into the engagement target portion 711 of the first engagement instrument 710.

The operator inserts the engagement target portion 711 of the first engagement instrument 710 into the mouth side A1 of the large intestine, and performs purse-string suture in a projecting state of the engagement target portion 711, thereby forming a suture portion A11. An outer surface of the suture portion A11 has a shape partially projecting to a projection side due to the suture.

Next, as illustrated in FIG. 7, the operator disposes the adhesion promotion device 100 between the mouth side A1 of the large intestine and the anal side A2 of the large intestine. The operator disposes the adhesion promotion device 100 so that the plurality of projection portions 31 formed on the rear surface 23 of the adhesion promotion portion 20 in the main body portion 10 come into contact with the suture portion A11 on the mouth side A1 of the large intestine. Then, the operator causes the engagement target portion 711 included in the first engagement instrument 710 to pass through the insertion hole 41 formed in the insertion portion 40 of the main body portion 10. In this manner, the insertion portion 40 can at least partially generate the sliding resistance with respect to the joining device 700 inserted into the insertion hole 41. Therefore, the main body portion 10 can increase the holding force with respect to the joining device 700 inserted into the insertion hole 41 by the insertion portion 40. Therefore, while the medical procedure is performed, the operator can help prevent the adhesion promotion device 100 from falling out of the engagement target portion 711.

Next, as illustrated in FIG. 8, the operator brings the plurality of projection portions 31 formed in the main body portion 10 into contact with the suture portion A11 on the mouth side A1 of the large intestine. The distal end of the plurality of projection portions 31 is disposed so that the distal end can partially penetrate the front surface tissue of the suture portion A11. In this manner, the plurality of projection portions 31 can at least partially generate the sliding resistance with respect to the front surface tissue of the suture portion A11. Therefore, the main body portion 10 can increase the holding force with respect to the biological organ serving as the joint object by the plurality of projection portions 31. Therefore, while the medical procedure is performed, the operator can help prevent the adhesion promotion device 100 from falling out of the suture portion A11, and can rather effectively reduce the risk factors of the anastomotic leakage of the biological organ. The operator may dispose the adhesion promotion device 100 on the anal side A2 of the large intestine by causing the engagement pin 721 included in the second engagement instrument 720 to pass through the insertion hole 41 formed in the insertion portion 40 of the main body portion 10.

Figure 9:
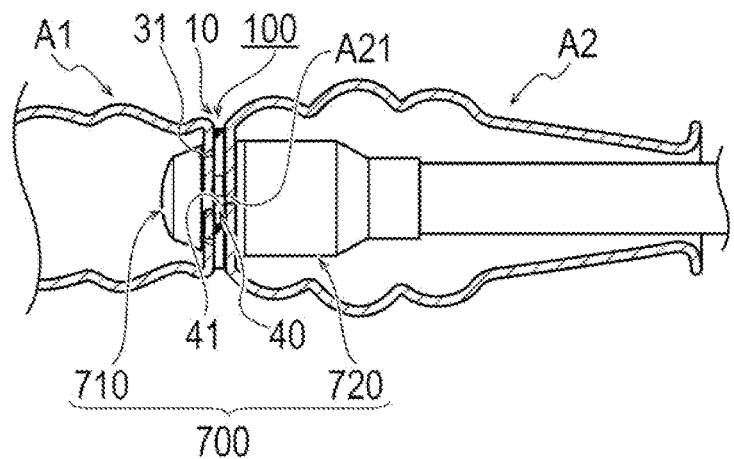
FIG. 9 is a schematic cross-sectional view for describing the large intestine anastomosis.

Next, while the operator maintains a state where the main body portion 10 is held with respect to the mouth side A1 of the large intestine by the holding portion 30, the operator engages the first engagement instrument 710 and the second engagement instrument 720 with each other by moving the first engagement instrument 710 and the second engagement instrument 720 to be relatively closer to each other as illustrated in FIG. 9. The operator pinches the mouth portion periphery on the mouth side A1 of the large intestine, the main body portion 10 of the adhesion promotion device 100, and the periphery of the through-hole A21 formed on the intestinal wall on the anal side A2 of the large intestine, between the first engagement instrument 710 and the second engagement instrument 720. The operator causes the joining device 700 to excise a portion on the mouth side A1 of the large intestine, a portion of the main body portion 10 of the adhesion promotion device 100, and a portion on the anal side A2 of the large intestine pinched between the first engagement instrument 710 and the second engagement instrument 720. In addition, at the same time, the operator operates the joining device 700 to join the peripheries of the excised site by using a stapler (not illustrated).

Next, as illustrated in FIG. 10, the operator removes the joining device 700 outward of the living body from the anal side A2 of the large intestine via an anus, for example. In this case, the operator causes the joining device 700 to excise most of the plurality of projections 31 of the main body portion 10 disposed in the region E2 located inward of the region E1 where the first engagement instrument 710 and the second engagement instrument 720 face and overlap each other across the main body portion 10, and where the biological organs joined by the joining device 700 are punched, and can remove most of the plurality of projections 31 outward of the living body together with the joining device 700. The adhesion promotion portion 20 of the main body portion 10 disposed outward of the region E2 where the biological organs joined by the joining device 700 are punched indwells the living body in a state of being pinched between the mouth portion periphery on the mouth side A1 of the large intestine and the intestinal wall on the anal side A2 of the large intestine. Therefore, the adhesion promotion device 100 can reliably fulfil a function of promoting the adhesion with respect to the mouth portion periphery on the mouth side A1 of the large intestine and the intestinal wall on the anal side A2 of the large intestine which serve as the joint objects by using the adhesion promotion portion 20 of the main body portion 10.

According to this treatment method, a relatively simple method of pinching the sheet-shaped main body portion included in the adhesion promotion device between one joint target site and the other joint target site is used. In this manner, it is possible to reduce the risk factors of the anastomotic leakage after a medical procedure for joining (for example, anastomosis for a digestive tract).

In addition, the adhesion promotion device 100 when in use increases the holding force of the main body portion 10 with respect to the biological organ serving as the joint object by the holding portion 30. Accordingly, when the operator operates the adhesion promotion device 100 (when the adhesion promotion device 100 indwells the body), the operator can help prevent the adhesion promotion device 100 from falling out of the biological organ. In addition, the adhesion promotion device 100 increases the holding force of the main body portion 10 with respect to the joining device 700 by the insertion portion 40. Accordingly, when the operator operates the adhesion promotion device 100 (when the adhesion promotion device 100 indwells the body), the operator can help prevent the adhesion promotion device 100 from falling out of the joining device 700. Therefore, it is possible to reduce the risk factors of the anastomotic leakage after surgery.

The detailed description above describes versions of an adhesion promotion device representing examples of the inventive medical device disclosed here. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An adhesion promotion device, the adhesion promotion device comprising:
    a main body portion configured to be disposed between biological organs serving as an object to be joined, the main body portion including a first region and a second region, the second region formed along an outer edge of the first region;
    the second region includes an adhesion promotion portion configured to promote adhesion of a biological tissue; and
    the first region includes a holding portion having a holding force with respect to the biological organs which is stronger than that of the adhesion promotion portion.

2. The adhesion promotion device according to claim 1, wherein the holding portion is integrally formed at a portion of an outer surface of the main body portion.

3. The adhesion promotion device according to claim 1, wherein the holding portion is separate from the main body portion, and is connected to a portion of the outer surface of the main body portion while covering the portion of the outer surface of the main body portion.

4. The adhesion promotion device according to claim 1, wherein the holding portion includes at least one projection.

5. The adhesion promotion device according to claim 1, wherein the main body portion further has an insertion portion formed of an elastic member, and the insertion portion further has an insertion hole into which a medical instrument is inserted.

6. The adhesion promotion device according to claim 1, wherein
    the main body portion is configured to be disposed in one joint target site of the biological organs serving as the object to be joined;
    the second region is configured to be joined to the biological tissue by a medical instrument including a first engagement instrument configured to be disposed in one joint site of the biological organs and a second engagement instrument configured to be disposed in an other joint target site of the biological organs and facing the first engagement instrument; and when the main body portion is configured to be joined to the biological tissue by the first engagement instrument and the second engagement instrument, the first region is located inward of a region where the first engagement instrument and the second engagement instrument face and overlap each other across the main body portion.

7. The adhesion promotion device according to claim 1, wherein the first region includes an adhesion promotion portion formed of a biodegradable sheet having a plurality of through-holes that pass through the first region and configured to promote adhesion of a biological tissue.

8. The adhesion promotion device according to claim 1, wherein the second region is formed of a biodegradable sheet having a plurality of through-holes that pass through the second region and configured to be promote the adhesion of the biological tissue.

9. The adhesion promotion device according to claim 1, wherein the holding portion has a friction portion configured to be disposed in the biological organs, the friction portion including a coating agent to which a particulate substance is added to generate a sliding resistance with respect to the biological organ serving as the object to be joined.

10. An adhesion promotion device configured to promote adhesion between biological tissue, the adhesion promotion device comprising:
    a main body portion made of biodegradable sheet configured to promote adhesion of the biological tissue, the main body portion configured to be disposed between biological organs serving as an object to be joined, the main body portion including a first region and a second region, the second region formed along an outer edge of the first region;
    the second region being formed of a biodegradable sheet having a plurality of through-holes that pass through the second region and includes an adhesion promotion portion configured to promote adhesion of a biological tissue; and
    the first region includes one or more projections having a holding force with respect to the biological organs which is stronger than that of the adhesion promotion portion.

11. The adhesion promotion device according to claim 10, wherein the holding portion is integrally formed at a portion of an outer surface of the main body portion.

12. The adhesion promotion device according to claim 10, wherein the holding portion is separate from the main body portion, and is connected to a portion of the outer surface of the main body portion while covering the portion of the outer surface of the main body portion.

13. The adhesion promotion device according to claim 10, wherein the main body portion further has an insertion portion formed of an elastic member, and the insertion portion further has an insertion hole into which a medical instrument is inserted.

14. The adhesion promotion device according to claim 10, wherein
    the main body portion is configured to be disposed in one joint target site of the biological organs serving as the object to be joined;
    the second region is configured to be joined to the biological tissue by a medical instrument including a first engagement instrument configured to be disposed in one joint site of the biological organs and a second engagement instrument configured to be disposed in an other joint target site of the biological organs and facing the first engagement instrument; and
    when the main body portion is configured to be joined to the biological tissue by the first engagement instrument and the second engagement instrument, the first region is located inward of a region where the first engagement instrument and the second engagement instrument face and overlap each other across the main body portion.

15. The adhesion promotion device according to claim 10, wherein the first region includes an adhesion promotion portion formed of a biodegradable sheet having a plurality of through-holes that pass through the first region and configured to promote adhesion of a biological tissue.

16. A method of promoting adhesion between biological tissue comprising:
    disposing an adhesion promotion device including a sheet-shaped main body portion that promotes the adhesion of the biological tissue between one joint target site and an other joint target site of an object to be joined of the biological organ; and
    joining the one joint target site and the other joint target site to each other in a state where at least a portion of the main body portion of the adhesion promotion device is disposed between the one joint target site and the other joint target site,
    wherein the main body portion includes a first region and a second region, the second region formed along an outer edge of the first region, and the second region includes an adhesion promotion portion that promotes adhesion of a biological tissue; and the first region includes a holding portion having a holding force with respect to the biological organs which is stronger than that of the adhesion promotion portion.

17. The method according to claim 16, further comprising:
    disposing the adhesion promotion device between a mouth portion periphery of a large intestine and an intestinal wall of the large intestine;
    moving the mouth portion periphery of the large intestine and the intestinal wall of the large intestine to be relatively closer to each other;
    placing the main body portion of the adhesion promotion device between the mouth portion periphery of the large intestine and the intestinal wall of the large intestine;
    joining the mouth portion periphery of the large intestine and the intestinal wall of the large intestine to each other in a state where the main body portion of the adhesion promotion device is placed between the mouth portion periphery of the large intestine and the intestinal wall of the large intestine; and
    causing the main body portion of the adhesion promotion device to indwell between the mouth portion periphery of the large intestine and the intestinal wall of the large intestine.

18. The method according to claim 16, wherein the holding portion is integrally formed at a portion of an outer surface of the main body portion.

19. The method according to claim 16, wherein the holding portion is separate from the main body portion, and is connected to a portion of the outer surface of the main body portion while covering the portion of the outer surface of the main body portion.

* * * * *